(12) United States Patent
Branton

(10) Patent No.: US 11,266,382 B2
(45) Date of Patent: Mar. 8, 2022

(54) TISSUE CASSETTE/BLOCK FILE POSITION FLAG AND METHOD RELATED THERETO

(71) Applicant: Brian L. Branton, Palmetto, FL (US)

(72) Inventor: Brian L. Branton, Palmetto, FL (US)

(*) Notice: Subject to any disclaimer, the term of this patent is extended or adjusted under 35 U.S.C. 154(b) by 0 days.

(21) Appl. No.: 16/509,449

(22) Filed: Jul. 11, 2019

(65) Prior Publication Data

US 2021/0007722 A1    Jan. 14, 2021

(51) Int. Cl.
| | | |
|---|---|---|
| *G01N 1/00* | (2006.01) | |
| *A61B 10/00* | (2006.01) | |
| *B01L 3/00* | (2006.01) | |
| *G01N 1/36* | (2006.01) | |
| *G01N 1/30* | (2006.01) | |

(52) U.S. Cl.
CPC ........ *A61B 10/0096* (2013.01); *B01L 3/5085* (2013.01); *G01N 1/30* (2013.01); *G01N 1/36* (2013.01); *B01L 2300/02* (2013.01); *B01L 2300/06* (2013.01); *G01N 2001/305* (2013.01); *G01N 2001/366* (2013.01); *G01N 2001/368* (2013.01)

(58) Field of Classification Search
None
See application file for complete search history.

(56) References Cited

U.S. PATENT DOCUMENTS 7,829,028 B2 * 11/2010 Elsener .................. G01N 1/312
422/536

* cited by examiner

*Primary Examiner* — Jyoti Nagpaul

(57) ABSTRACT

A flag, or marker for identifying the locations of a plurality of tissue cassettes containing mounted Formalin Fixed Paraffin Embedded (FFPE) tissue specimens once removed from a tissue cassette/block storage system. The invention comprises a rectangular cuboid body member having front, rear, left, right, top, and bottom surfaces which substantially approximates the shape of a predefined number of tissue cassette/blocks, with a recessed area with grooves to accept one tissue index marker card for recording the patient's case information, or other relevant information. When multiples of the present invention are used within a tissue cassette/block storage system, they point to locations where pluralities of tissue cassette/blocks should be returned, and provides a support structure for neighboring tissue cassette/blocks within the storage location from becoming askew or damaged within the tissue cassette/block storage system.

5 Claims, 3 Drawing Sheets

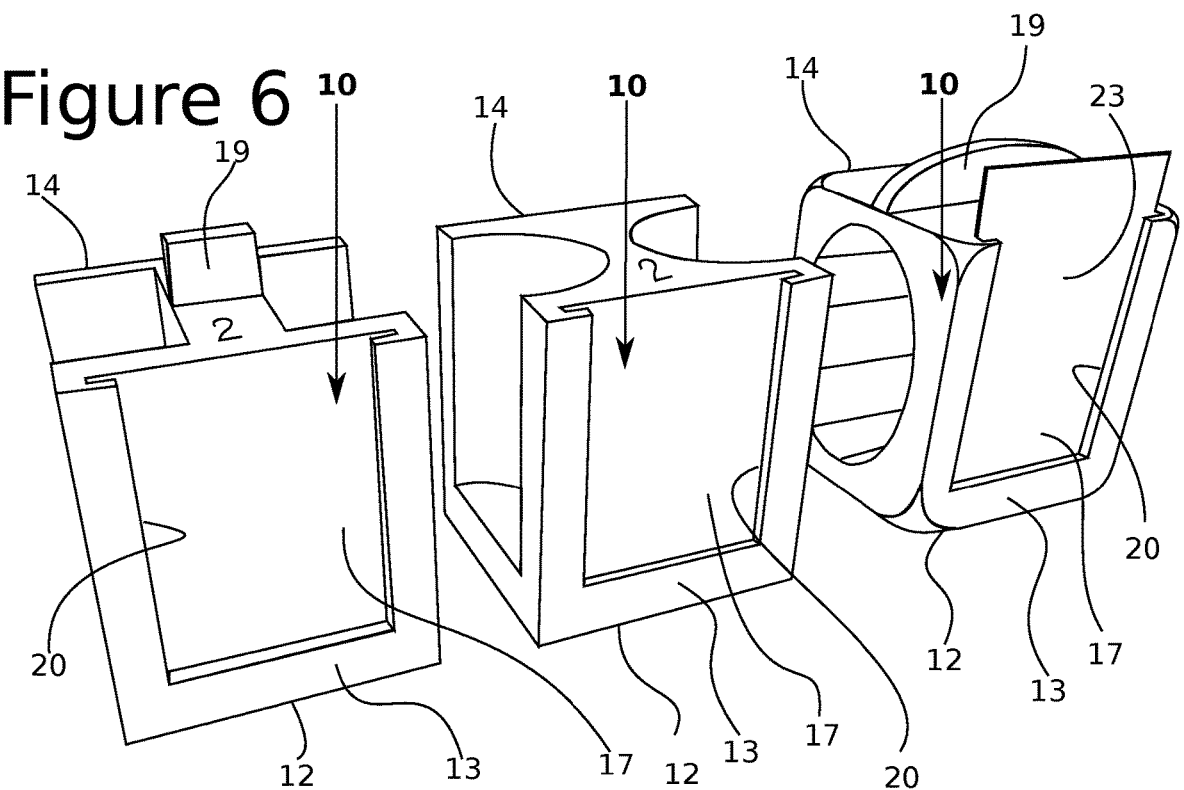
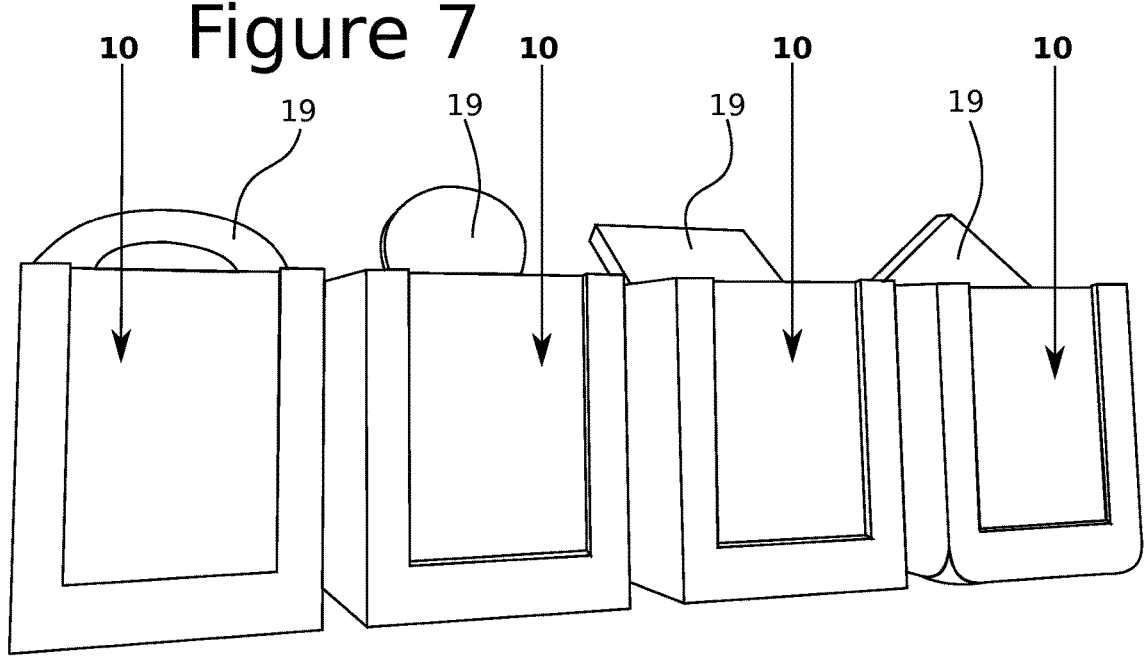

TISSUE CASSETTE/BLOCK FILE POSITION FLAG AND METHOD RELATED THERETO

BACKGROUND OF THE INVENTION

Within the field of Pathology, Formalin Fixed Paraffin Embedded (FFPE) tissue blocks or more commonly known as "tissue blocks", refers to the process of preserving human or animal medical tissue specimens by exposure to Formaldehyde solutions, followed by embedding the preserved tissue into a block of paraffin wax. FFPE tissue blocks are utilized far and wide in the diagnosis and treatment of diseases.

The method of producing FFPE tissue blocks, or "tissue blocks", from excised tissue samples is a complicated, and time consuming process, and is beyond the scope of this application; however a brief description is required for an understanding of the invention presented herein. Within the medical industry a human patient who undergoes a biopsy procedure has a sample of tissue excised, or removed from their personage. Biopsy samples are sent to Pathology laboratories where laboratory staff dissect these tissue samples in order to maximize the exposure of a particular abnormality, or point of interests in the tissue. The tissue samples are then cut down to fit within tissue cassettes. These cassettes are small plastic boxes with attached lids, and small holes incorporated into the body of the cassettes to allow chemicals to flow throughout the internal cavities, and bathe the tissue with specific chemicals. At some point the patient's data is written or "engraved" onto the plastic base cassette with all the relevant medical information for future reference. The tissue cassette lid is closed, and the cassette is immersed into Formaldehyde solution baths to inhibit putrefaction, or autolysis, and to maintain the proteins and structural integrity of the tissue. Groups of these tissue cassettes are placed into a "vacuum infiltration" processor (VIP) machines, that processes the tissue samples with heat, and vacuum, to dehydrate, and then re-hydrates the tissue by replacing water with molten paraffin wax inside the samples. This process can take several hours and these machines are often computer controlled, which does not require human intervention. When the tissue samples have been sufficiently re-hydrated they are removed from the VIP machines. The plastic cassettes are opened and the tissue sample is inserted into a metal mold, and orientated to maximize the exposure of the tissue's point of interest during the Microtomy procedure. The empty space within the mold is filled with additional molten paraffin to entomb the tissue sample inside a block of paraffin. This process is known as "embedding" the tissue sample. Lastly, the lids are removed from the plastic cassettes and discarded, the base cassette is inserted on top of the corresponding molded tissue, and additional paraffin is added to the cassette to lock the molded "block" onto the plastic base cassette. Once the tissue samples have been "embedded" the process continues to microtomy where microscope slides are created, and then stained to highlight the tissue's structural detail. These microscope slides are reviewed by medical personnel via microscopy procedures, at which point a determination is made to the course of treatment required for a particular patient.

By virtue of the patient's lives affected, and the uniqueness of each tissue biopsy, all are irreplaceable. Medical facilities are governed by rules and regulations, in which every single tissue block must be accounted for. Hence, complicated storage, filing, and tracking systems are implemented to account for every tissue block. By utilizing industry standards, or agreed upon classification systems, once a tissue block has been processed and a medical determination has been made to the patient's course of actions, the tissue blocks are filed into a tissue block storage system for long term storage, future reference, or referrals.

Within prior art the preferred method of storing tissue blocks for long term storage is laterally within drawers/cabinets or in box type containers providing vertical orientation, whereby the blocks are inserted standing on one end of the plastic cassette within the drawer or box. The tissue blocks are positioned front to back within rows, drawers, or containers. The vertical orientation provides quick viewing of specimen data printed on the plastic cassette and easy access and retrieval of the tissue blocks.

When tissue blocks are inserted into block storage systems the physical inclination of unsupported tissue blocks are to fall forward, or backwards, depending upon gravity, and other forces. A standard practice is to insert pieces of closed cell foam between, or behind, the tissue blocks to provide support, or prevent the tissue blocks from laying down flat, or reclining upon a neighboring tissue block. A multitude of tissue blocks are required to fill the entire drawer row.

As with all storage systems, medical librarians withdraw a plurality of tissue blocks from their respective locations to further process additional specimen for microscopy review, or as part of outside pathological consultation or review. The length of time that these tissue blocks remain withdrawn depends upon what action is being pursued in the course of care. Traditionally, when tissue blocks are removed from their storage system, the librarian transcribes the particular specimen information onto a block index marker card, and it is inserted into the area from whence the tissue blocks were removed. These block index marker cards are made from card stock paper or paper board, and may incorporate pre-printed lines for recording the particular patient's case information or the destination of the tissue blocks removed for future reference.

The plastic tissue cassettes detailed above are produced in multitudes of variations in size, form, and designs. All tissue cassettes have a base cassette with a corresponding lid either attached or separate. The standard tissue cassette measures 41×30×6 mm, or 1⅝"×1⅛"×¼", and is offered in a plurality of color, and function. Standard tissue cassettes are used with the typical biopsy, or dissected tissue specimen, because of the number and size of the slots, which measure 1×5 mm per slot with a total of 128 slots within each base cassette. The lid also incorporates these same slots within its member. These slots are designed to allow the reagents to flow in and around the tissue specimen during the Vacuum Infiltration process. The slots also offer a lattice structure to support the specimen during the Microtomy process. Other cassettes offered are biopsy, and compartment cassettes each offering their own features used during the infiltration process. Mega-Cassettes are another cassette used within the medical industry. As the name implies, these cassettes are for much larger tissue specimens, and offer the same features as a standard tissue cassette. All cassettes are produced in myriads of colors to allow the laboratory technician to discern different specimens or processing procedures.

SUMMARY OF THE INVENTION

For a further understanding of the nature, and objectives of the present invention, reference should be made to the detailed description, taken in conjunction with the accompanying drawings. The present invention fulfills the following role: When a multitude of tissue blocks are removed from specimen tissue block storage systems, as the void is created by the removal of the tissue blocks, the remaining blocks tend to lean against other remaining tissue blocks held within the drawer. If a sufficient number of tissue blocks are removed the remaining tissue blocks encumber further removal of additional blocks. As stated before, block index marker cards, (card stock markers), are inserted into the void created by the removal of the tissue blocks, which marks the location of the withdrawn blocks, but provides no physical presence to fill the void. Pieces of closed cell foam can be utilized for support, but offer no informational detail about the tissue blocks removed. Additionally, the act of opening and closing the drawer can dislodge the index marker cards if left unsupported. These cards should be well seated down against the remaining blocks to prevent accidental dislodging. By using the invention, the tissue block file position flag marker, the body member of the invention is inserted into the void created by the removal of the tissue blocks. The present invention will be made in a plurality of depths, and depended upon the number of tissue blocks withdrawn, the librarian would insert a corresponding sized tissue block file position flag marker equal to the number of tissue blocks removed to fill the void. Multiple tissue block file position flag markers can be utilized together to fill larger voids. Once the void is filled the remaining tissue blocks would safely recline against the body of the invention, thus preventing the remaining tissue blocks from falling flat, or encumbering other tissue blocks. Being made from brightly colored plastics, the tissue block file position flag marker would be easily visible against the remaining tissue blocks. Once the librarian returns with the previously removed tissue blocks, the invention flagging the location, would prompt a quick return of the removed tissue blocks.

BRIEF DESCRIPTION OF DRAWINGS

FIG. 6 is a perspective view illustrating variations of the present invention that incorporates differences into the body member surfaces (10).

FIG. 7 is a perspective view illustrating variations of the handle (19) elements for the present invention.

DETAILED DESCRIPTION OF PREFERRED EMBODIMENT

Figure 1:
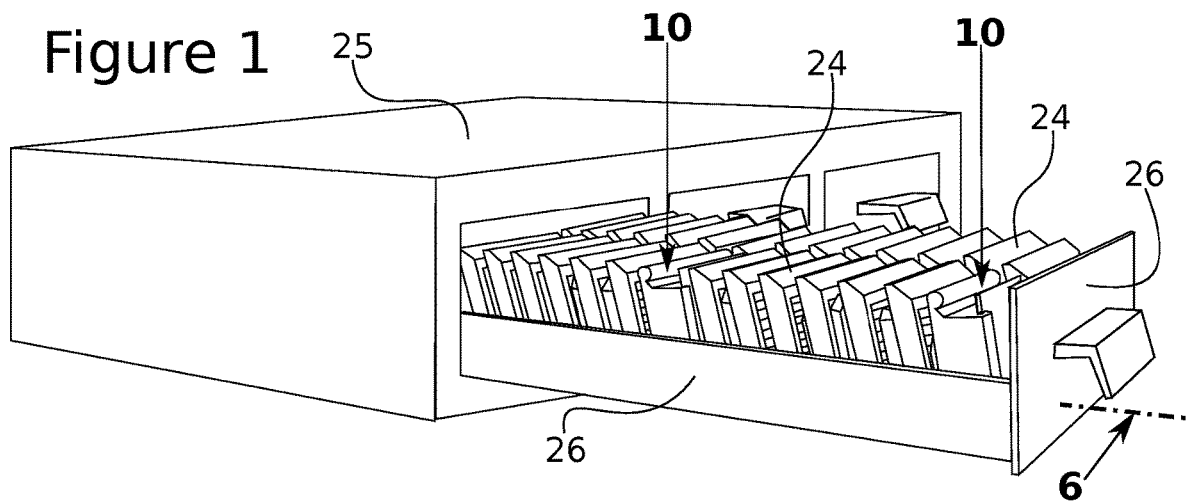
FIG. 1 is a perspective view of an exemplary embodiment of two tissue block file position flags markers in use within a representative tissue block storage cabinet and drawer.

Referring to the drawings, numeral (10) designates one embodiment of one tissue block file position flag marker or the present invention (10) comprise a unitary molded plastic rectangular cuboid block that measures longer in length than one tissue cassette, narrower in width than one tissue cassette, with the depth equal to the thickness of a specified plurality of tissue base cassettes and corresponding molded biopsy specimens, an integrated handle, and a recessed slot or groove for one block index card.

In FIG. 1 the tissue block file position flags markers (10), or the present invention are illustrated in combination with a tissue block filing cabinet (25), positioned within a tissue block filing drawer (26), and the surrounding tissue blocks (24) contained therein. The bodies (10) of the present invention are inserted to fill the void created when a group of Patient's tissue blocks are removed from their storage locations as part of the continuing medical care.

Figure 2:
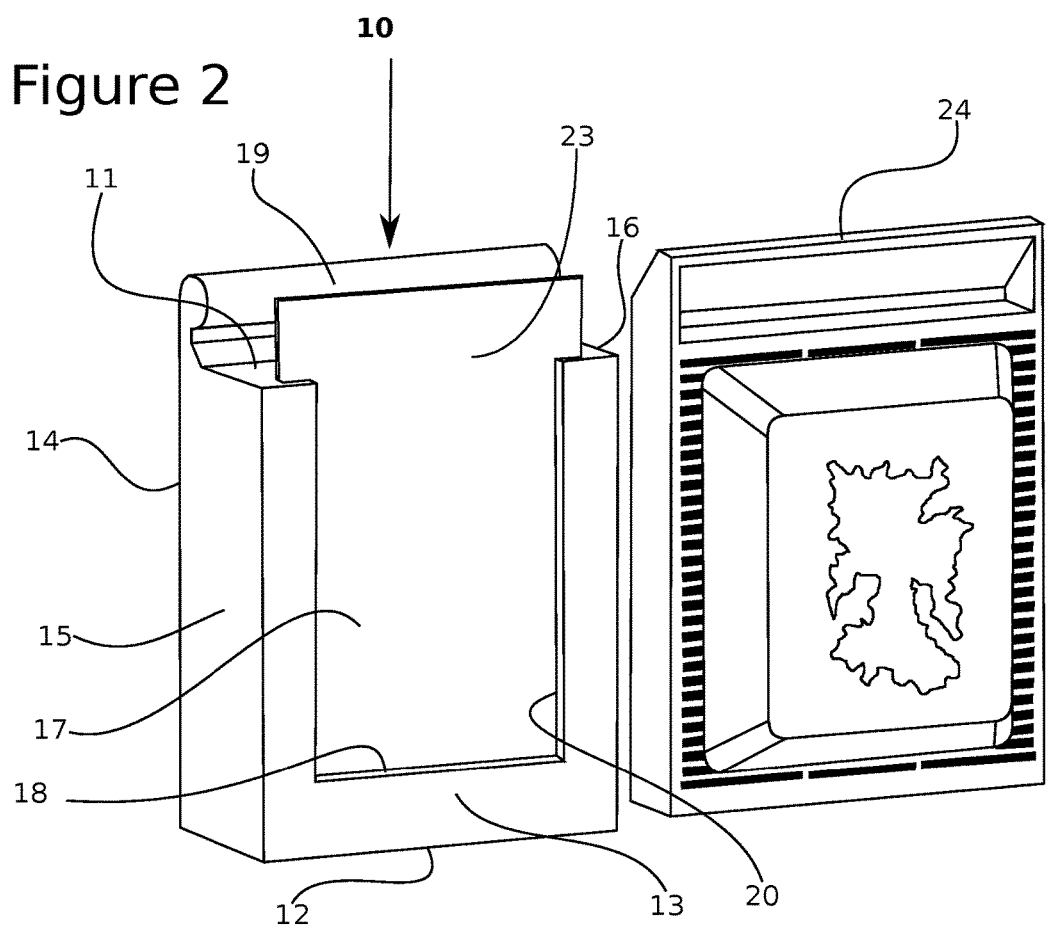
FIG. 2 is a perspective view of one embodiment of the present invention adjacent to a tissue specimen block for a size comparison.

Referring to FIG. 2, the tissue block file position flags markers (10) hereto pictured as the embodiment of the invention is illustrated adjacent to a tissue specimen block (24) for a size comparison. The present invention (10) hereto pictured as the embodiment with a preferably rectangular top surface (11), a rectangular bottom surface (12), parallel and spaced apart from the top surface (11), a rectangular front surface (13), a rectangular rear surface (14), parallel to and spaced apart from the front surface (13), a rectangular left surface (15) a rectangular right surface (16), wherein the left surface (15) is parallel and spaced apart from the right surface (16), The front surface (13) has a rectangular area (17) displaced parallel to the front surface (13) forming the inner surface (17). Extending outwardly from opposite outer edges of the inner surface are substantially identical mirrored ends (18) forming channels with the front surface (13), whereby these channels (20) slidably receive a tissue index marker card (23) within the slot or groove, where the top surface (11) incorporates a handle (19) extending above the flag body (10) for grasping the present invention, or tissue block file position flags markers (10).

Figure 3:
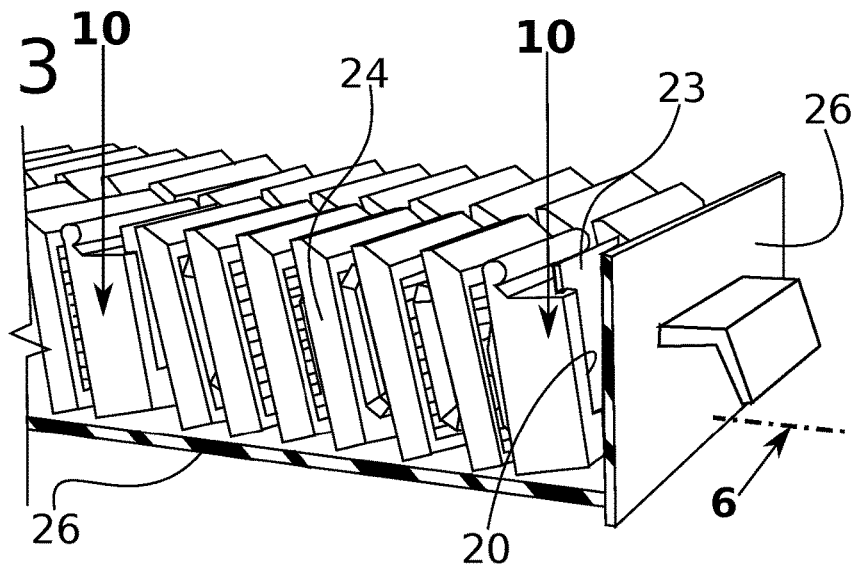
FIG. 3 is a vertical cross-sectional view of the drawer of FIG. 1 taken along line 6.

Referring to FIG. 3 illustrates a cross-sectional view of the tissue block storage drawer (26), from the tissue block filing cabinet (25) in FIG. 1, following along line (6), showing generally the contents of the tissue block file drawer, which denotes a plurality of tissue blocks (24) arranged in rows in a "front to back" orientation, whereby the tissue block file position flag markers (10) are engaged with and supporting the surrounding tissue blocks (24). The tissue block file position flag marker (10) is capable of such positioning as it is not dependent upon the agreed classification systems utilized to file the tissue blocks within the storage system. The corresponding patient's information is recorded upon the block index marker card (23) which is inserted into the groove (20) on the tissue block file position flag marker's body (10), for the represented "removed" tissue blocks.

Figure 4:
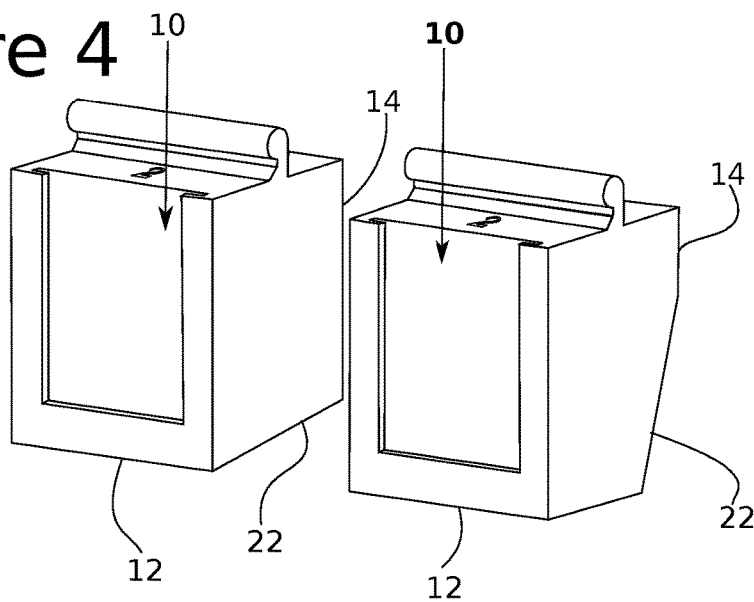
FIG. 4 is a perspective view illustrating two embodiments of the tissue block file position flag marker's body member that incorporates a wedged surface (22) into the bottom (12) and rear surfaces (14).

Referring to FIG. 4 illustrates variations in two embodiments of the present invention (10), whereby the tissue block file position flag marker represented on the left, incorporates the wedged surface (22) into the bottom surface (12), which allows the invention's body (10) to recline backward slightly. This recline is similar to the natural tendencies of unsupported blocks to recline held within a drawer structure. The wedged surface (22) would follow this tendency to recline backwards thus preventing damage to the valuable tissue blocks. In the illustration, the representation of the invention's body (10) on the right has a wedged surface (22) incorporated into the rear surface (14), the addition of the wedged surface (22) reduces the bottom surface (12) allowing the tissue block file position flag marker body (10) to be inserted into voids where the surrounding tissue blocks have moved within the storage drawer reducing the overall space or gap within the drawer. The wedged surface (22) allows the invention's body (10) to support the remaining tissue blocks correcting the required spacing.

Figure 5:
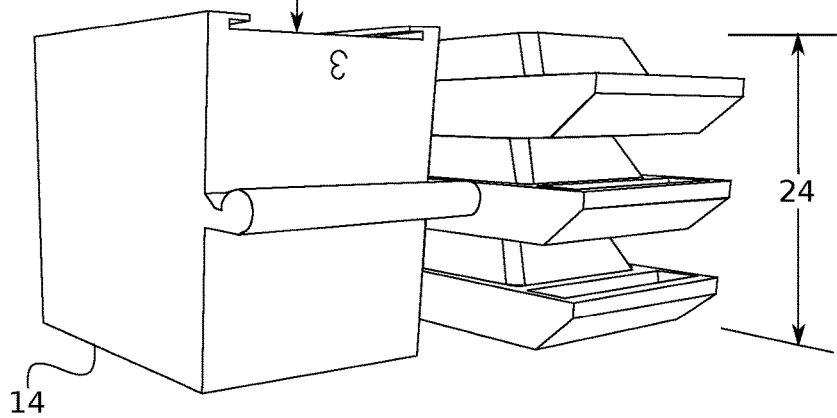
FIG. 5 is a perspective view of a embodiment of the present invention (10), positioned upon its back surface, with a comparable stack of tissue blocks (24) to show the thickness of the present invention.

Referring to FIG. 5 illustrates one embodiment of the present invention (10), positioned upon its back surface (14), adjacent to a representation of corresponding stacks of three tissue blocks (24) to provide a reference that the tissue block file position flag marker (10) is equal to a set number of like tissue blocks (24). Each tissue block file position flag marker (10) is embossed, engraved, or labeled with a number designating the thickness of tissue blocks represented by the body of the present invention.

Referring to FIG. 6 the present invention (10) is shown in a plurality of forms where the entire body member of the tissue block file position flag marker (10) is reduced to the front surface (13), rear surface (14), bottom surface (12), recessed surface (17), groove (20) for the tissue index marker card card (23), and the handle (19) as primary surfaces needed to maintain the correct structural elements. The other surfaces have been reduced to minimal proportions to provide structural elements to the primary surfaces. The three variations represented are example modifications and may not be reflected in the final embodiment.

FIG. 7 illustrates four variations of the present invention, or body members of the tissue block file position flag marker (10), with modifications to the handle (19) member utilized when inserting and removing the body member from a storage location. The four examples shown are only a few of the conceivable variations to the handle (19) member possible, and may not reflect upon the final embodiment.

Today, the universal use of FFPE tissue blocks is well beyond the scope of the present invention. It is the intent for the tissue block file position flag marker (10) to fulfill the role in which it has been described and detailed herein. Although the aforementioned interpretation of the present invention will be offered with variations in its design and function, the final embodiment, without departing from the spirit and scope, will universally provide a means whereby persons utilizing this invention might ultimately ease their daily routines when interacting with tissue block storage systems with the use of the tissue block file position flag marker (10) as hereinafter claimed.

REFERENCES CITED

Williamson, G. inventor; Card index marker. U.S. Pat. No. 770,788. 1904 Sep. 27.
Rand, J., inventor; Card Index. U.S. Pat. No. 1,294,948. 1919, Feb. 18.
Crystal, S. inventor; Space indicator for filing system. U.S. Pat. No. 1,485,169. 1924 Feb. 26.
Andersson, A. inventor; Indicator device for filing drawers. U.S. Pat. No. 1,596,225. 1926 Aug. 17.
Weiskopf, E.; Gioia, C., inventors; Technicon International Ltd. assignee. Mount for paraffin-blocked hitologic tissue specimen. U.S. Pat. No. 2,868,072. 1959 Jan. 3.
McCormick, J., inventor; Embedding structure and method. U.S. Pat. No. 2,996,762. 1961 Aug. 22.
Schachat, E. inventor; Sherwood Medical Industries, Ltd, assignee; Method of embedding a histology specimen. U.S. Pat. No. 3,996,326. 1976 Dec. 7.
White, F., inventor; Mile Laboratories, Inc., assignee; Biological specimen process apparatus and cover member therefor. U.S. Pat. No. 4,034,884. 1977 Jul. 12.
Beall, G.; Noonan, R. inventors; Miles Laboratories, Inc. assignee; Biological specimen process apparatus. U.S. Pat. No. 4,220,252. 1980 Sep. 2.
Schultz, R.; Graham, D., inventors; Allied Corporation, assignee; Biological tissue cassette. U.S. Pat. No. 4,421,246. 1983 Dec. 20.
Trendler, D. inventor; Maclean-Fogg Company, assignee; Hinged tissue cassette apparatus. U.S. Pat. No. 4,549,670. 1985 Oct. 29.
Dudek, P. inventor; Unitary biological specimen processing apparatus. U.S. Pat. No. 4,997,100. 1991 Mar. 5.
Carney, J., inventor; File position location device and method related thereto. U.S. Pat. No. 5,836,098. 1998 Nov. 7.
Occhipinti, V; Occhipinti P.; Occhipinti, S., inventors; A.I.P. Products, Inc, assignee; File marker U.S. Pat. No. 5,942,293. 1999 Aug. 24.
Lafond, A.; Bertin, Y inventors; 3088081 Canada Inc. assignee; Biological specimen cassette. U.S. Pat. No. 6,176,383 B1. 2001 Jan. 23.
Cummings, A., inventor; File/Book place marker system. U.S. Pat. No. 6,354,027 B1. 2002 Mar. 12.
Laudat, A. inventor; Cassette stack having cassettes for histological preparations. U.S. Pat. Application 2002/0125166 A1. 2002 Sep. 12.
Hunnell, J. inventor; Unitary assembly of biological specimen support articles, and apparatus for dispensing individual biological specimen support articles therefrom. U.S. Pat. Application 2005/0152809 A1. 2005 Jul. 14.
Williamson, W. inventor; Prefix tissue cassette. U.S. Pat. Application 2007/0116612 A1. 2007 May 24.
McCormick, J., inventor; Leica Biosystems Richmond, Inc., assignee; Histological specimen cassette. U.S. Pat. No. 7,987,564 B2. 2011 Apr. 19.
Britz, T. inventor; Primera Technology, Inc. assignee; Histological specimen cassette. U.S. Pat Application 2013/0224088 A1. 2013 Aug. 29.
Webber, P; Webber, P.; Titcombe, R. inventors; CellPath Ltd. Assignee; Cassette. U.S. Pat. No. 9,594,087 B2. 2017 Mar. 14.
Webber, P.; Webber, P.; Titcombe, R. inventors; CellPath Ltd. Assignee; Histology cassette stack. U.S. Pat. No. 10,288,536 B2. 2019 Mar. 14.

What is claimed is:

1. A method of use a plurality of tissue cassette/block file position flag marker comprising the steps of:
    a. locating and removing a plurality of tissue blocks containing affixed FFPE tissue specimens from a location inside a tissue block storage container held within a tissue block storage system;
    b. counting a plurality of tissue blocks removed to determine the correct sized one ogf the plurality of flag markers needed to infill the space by the tissue blocks removed;
    c. selecting a correctly sized one of the plurality of flag markers roughly equal to the plurality of tissue blocks removed;
    d. transcribing any relevant patient information from the plurality of tissue blocks removed, onto a tissue index marker card card, and then the tissue index marker card is inserted into the grooves on the face of the correct sized one of the markers;
    e. inserting the correct sized one of the flag markers into the location within the tissue blocks storage container, infilling the space created by removing the plurality of tissue blocks;
    f. returning a plurality of tissue blocks to the location, by removing the correct sized one of the flag markers and inserting the plurality of tissue blocks back into the location inside a tissue blocks storage container.

2. The method of claim 1, where the flag markers measure substantially tall enough in height to be seen behind other tissue blocks inside tissue block storage containers.

3. The method of claim 1, where the flag markers measure substantially short enough in height that the tissue block storage container can be closed inside a tissue block file storage system.

4. The method of claim 1, where the flag markers measure substantially in height whereby the marker is configured to be seen behind other tissue blocks and short enough that the tissue block file storage container can be closed inside the tissue block file storage system.

5. A tissue block file position flag marker comprising:
   a. a free-standing movable marker having a rectangular cuboid shape, that substantially approximates the physical dimensions of a predefined number of tissue blocks with FFPE mounted tissue specimens on each cassette, otherwise known as "tissue blocks", positioned to stand vertically on the surfaces opposite the slanted surfaces of the histological tissue cassette, and said slanted surfaces is known to contain patient information, or the cassette label areas facing forward and up, with each tissue block lined up in a row;
   b. the predefined number of tissue blocks corresponds to a predetermined number, in the form of one of 5, 10, 20, 25, and 50, or a different number of tissue blocks;
   c. a length of the marker is the distance between the front and rear surfaces spaced apart that substantially approximates the physical thickness measured front to back of the predefined number of tissue blocks standing vertically in a row;
   d. a width of the marker is the distance between the left and right surfaces spaced apart that substantially approximates a smaller measurement than a width of tissue blocks standing vertically in a row;
   e. a heigth of a marker is the distance between the top and bottom surfaces spaced apart that substantially approximates the length of tissue blocks standing vertically in a row;
   f. the front surface of a marker has an area displaced and parallel to the front surface forming an inner surface, extending outwardly from opposing outer edges of the left, and right surfaces and the inner surface are substantially indentically mirrored ends forming channels with the front surface, where the channel is configured to slidably receive a tissue index marker card, making the index card visible on the front surface;
   g. the top surface incorporates a handle extending above for grasping and positioning the marker inside the tissue block storage container;
   h. the predetermined number of predefined tissue blocks is embossed, engraved, or surfaced labeled with the corresponding number upon any surface of the marker.

* * * * *